(12) United States Patent
Yeh et al.

(10) Patent No.: US 8,691,908 B2
(45) Date of Patent: Apr. 8, 2014

(54) CARBON NANOMATERIAL-SUPPORTED CATALYST AND APPLICATION THEREOF IN CYCLIC CARBONATE SYNTHESIS

(75) Inventors: Cheng-Wei Yeh, Pingtung County (TW); Mao-Lin Hsueh, Pingtung County (TW); Kuo-Chen Shih, Kaohsiung (TW); Yi-Zhen Chen, Yilan County (TW)

(73) Assignee: Industrial Technology Research Institute, Hsinchu (TW)

( * ) Notice: Subject to any disclaimer, the term of this patent is extended or adjusted under 35 U.S.C. 154(b) by 244 days.

(21) Appl. No.: 13/224,095

(22) Filed: Sep. 1, 2011

(65) Prior Publication Data

US 2012/0165482 A1 Jun. 28, 2012

(30) Foreign Application Priority Data

Dec. 22, 2010 (TW) .............................. 99145161 A

(51) Int. Cl.
C08K 3/04 (2006.01)
C08F 2/00 (2006.01)

(52) U.S. Cl.
USPC ........................................... 524/496; 526/89

(58) Field of Classification Search
USPC ....................................................... 524/496
See application file for complete search history.

(56) References Cited

U.S. PATENT DOCUMENTS

| | | | |
|---|---|---|---|
| 6,933,394 B2 | 8/2005 | Sakakura et al. | |
| 7,241,496 B2 | 7/2007 | Chen et al. | |
| 7,357,909 B2 | 4/2008 | Le-Khae | |
| 7,501,531 B2 | 3/2009 | Van Kruchten et al. | |
| 7,728,164 B2 | 6/2010 | Lange | |
| 2004/0024227 A1 | 2/2004 | Sakakura et al. | |
| 2005/0070724 A1 | 3/2005 | Srinivas et al. | |
| 2007/0155910 A1 | 7/2007 | Stokes | |
| 2008/0287591 A1 | 11/2008 | Hwang et al. | |

FOREIGN PATENT DOCUMENTS

| | | |
|---|---|---|
| CA | 2 354 775 A1 | 6/2000 |
| CN | 1416952 A | 5/2003 |
| CN | 1944783 A | 4/2007 |
| CN | 101058418 A | 10/2007 |
| CN | 101181988 A | 5/2008 |
| CN | 101293885 A | 10/2008 |
| EP | 1359169 A2 | 11/2003 |
| JP | 2002-532446 A | 10/2002 |
| JP | 2003-251189 A | 9/2003 |
| JP | 2004-002849 A | 1/2004 |
| JP | 2009-057374 A | 3/2009 |
| JP | 2009-542565 A | 12/2009 |
| JP | 2010-502571 | 1/2010 |

OTHER PUBLICATIONS

Kawahara et al., Polymer Journal, vol. 41, No. 9, pp. 744-751, 2009.*
Chinese Offict Action for Chinese Application No. 201110148205.0 dated Mar. 19, 2013.
Japanese Office Action for Japanese Application No. 2011-0242432 dated Apr. 16, 2013.
Taiwan Office Action for Taiwan Application No. 99145161 dated Apr. 23, 2013.
Emily Baird Anderson, Synthesis and Non-Covalent Interactions of Novel Phosphonium-Containing Polymers, XP-002661634, Aug. 18, 2010, 125-150.

* cited by examiner

Primary Examiner — Hui Chin
(74) Attorney, Agent, or Firm — Muncy, Geissler, Olds & Lowe, P.C.

(57) ABSTRACT

The present disclosure is related to a carbon-nanomaterial-supported catalyst, including: a carbon nanomaterial, and a polymer grafted onto the carbon nanomaterial, wherein the polymer has a repeat unit containing a phosphonium salt and its molecular weight is 1,000-200,000. The disclosure is also related to a method of preparing carbonate, which includes using the carbon nanomaterial-supported catalyst for the cycloaddition reaction of carbon dioxide into the epoxy group.

11 Claims, No Drawings

CARBON NANOMATERIAL-SUPPORTED CATALYST AND APPLICATION THEREOF IN CYCLIC CARBONATE SYNTHESIS

CROSS REFERENCE TO RELATED APPLICATIONS

This application claims priority of Taiwan Patent Application No. 099145161, filed on Dec. 22, 2010, the entirety of which is incorporated by reference herein.

BACKGROUND OF THE INVENTION

1. Field of the Invention

The present disclosure relates to a catalyst for preparing carbonate, and more particularly to a carbon nanomaterial-supported catalyst including phosphonium salt polymers.

2. Description of the Related Art

Catalysts play an important role in the chemical synthesis industry. Catalysts may improve reaction activity and shorten the reaction time, thereby reducing production costs. Catalysts can be generally divided into two major categories, homogeneous and heterogeneous catalysts. Although homogeneous catalysts have advantages of high activity and good selectivity, recovery is not easy, thereby increasing production costs. On the other hand, although heterogeneous catalysts are easily separated and recover easily, activity and selectivity thereof are not satisfactory.

In the chemical synthesis industry, cyclic carbonate ester is an important class of compounds in the field of an electrolyte for lithium batteries. The green process of cyclic carbonate ester involves using an appropriate catalyst for the cycloaddition reaction of carbon dioxide and epoxide. For example, a propylene carbonate, an important ingredient of an electrolyte in a lithium battery, can be obtained from the reaction of propylene oxide and carbon dioxide in the presence of catalysts.

In the resin industry, a non-isocyanate resin (NIPU) can be derived from a monomer with a cyclic carbonate functional group. Because the synthesis method avoids using highly toxic isocyanate esters, such as NIPU resin can be regarded as a "green" material. In addition, the low toxic nature allows the non-isocyanate polyurethane to be applied in biomedical materials. The green process of cyclic carbonate ester compounds uses carbon dioxides and epoxy compounds as raw materials. The cyclic carbonate ester compounds are obtained from the cycloaddition reaction of carbon dioxide with the epoxy group by using catalyst systems including a Lewis base, an ionic liquid, a metal complex, a heterogeneous metal salt, a silica-supported catalyst, a porous metal oxide salt, or an ion exchange resin. Among the catalysts mentioned above, salt or ionic liquid catalyst is most common. However, the existing homogeneous and heterogeneous catalyst systems have some shortcomings. For homogeneous catalysts, the catalysts and the products are homogeneous, and hence they are not easily separated and more purification procedure. For heterogeneous catalysts for reactions, the conversion rate of reactions is not satisfactory, and more harsh reaction conditions, such as higher gas pressure, are usually required for the catalytic reactions.

US Patent Publication No. 2005/070724A1 provides a zeolite-based catalyst for preparing cyclic carbonate. The heterogeneous catalyst serves as a Lewis base, and converts an epoxide into a cyclic carbonate in the presence of carbon dioxide. However, the reaction needs to be maintained under a high carbon dioxide gas pressure and more harsh reaction conditions (>6 atm, 120° C.).

U.S. Pat. No. 7,728,164 provides a phosphonium bromide salt (tetraalkylphosphonium bromide) as a homogeneous catalyst, which catalyzes the synthesis reaction of a propylene carbonate in the presence of carbon dioxide. The phosphonium bromide salt catalyst also requires more harsh reaction conditions. (>19 atm, 180° C.)

U.S. Pat. No. 6,933,394 provides a method of using phosphonium iodine salt compounds for catalyzing the reaction of epoxides with carbon dioxide to produce cyclic carbonate. The reaction with the homogeneous catalyst requires higher gas pressure (>100 atm), and has a higher demand for production equipment, thus increasing production costs.

Accordingly, what is needed in the art is a catalysis system having advantages of high catalytic reactivity as homogeneous catalysts and easy separation and recovery as heterogeneous catalysts.

BRIEF SUMMARY OF THE INVENTION

The present disclosure provides a carbon nanomaterial-supported catalyst, comprising: (a) a carbon nanomaterial; and (b) a polymer grafted onto the carbon nanomaterial, wherein the polymer has a repeat unit containing a phosphonium salt and the polymer has a number average molecular weight of 1,000-200,000.

The present disclosure also provides a method of preparing cyclic carbonate, comprising: performing a cycloaddition reaction between a carbon dioxide and an epoxy compound in the presence of the above carbon nanomaterial-supported catalyst, to form a cyclic carbonate.

A detailed description is given in the following embodiments.

DETAILED DESCRIPTION OF THE INVENTION

The present disclosure relates to a carbon nanomaterial-supported catalyst, including a carrier and an active center. The carrier is a carbon nanomaterial including single-wall carbon nanotubes, multi-wall nanotubes, carbon nanofibers, carbon nanocapsules, active carbons, carbon blacks, or combinations thereof. The carbon nanomaterial is characterized by high surface area, and high mechanical strength, which provides the carbon nanomaterial-supported catalyst with an easy separation property as heterogeneous catalysts. The active center is a polymer containing phosphonium salts, wherein the cations of the phosphate salts are phosphonium cations, and the anions of the phosphate salts are halide ions. The phosphonium-containing polymer is grafted onto the surface of the carbon nanomaterial, such that, the polymer with phosphonium ligands is distributed over the surface of the carbon nanomaterial. The polymer has a repeat unit containing phosphonium salts, and has a number average molecular weight of 1,000-200,000, preferably 2,000 to 100,000. The ratio of the phosphonium groups grafted to the carbon nanomaterial is 0.001-150 mmol per gram of the carbon nanomaterial. The polymer has good solubility properties in common organic solvents. Since phosphonium groups are grafted onto the surface of the carbon nanomaterial, the carbon nanomaterial of the invention can be easily dispersed in an organic solvent. Therefore, the catalyst of the invention is able to maintain high selectivity and activity of a homogeneous catalyst, while being easy to separate and recover from the reaction system. The catalysts of the invention can be applied to the cycloaddition reaction of carbon dioxide and the epoxide to form a cyclic carbonate ester.

The polymer includes a repeat unit containing a phosphonium salt, and has preferably a general structure of formula I:

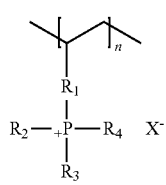

(I)

wherein $R_1$ represents $C_1$-$C_{10}$ alkylene, $C_3$-$C_8$ cycloolefin, $C_6$-$C_{12}$ arylene, an ester group, $C_3$-$C_8$ cycloalkene or $C_6$-$C_{12}$ arylene, wherein the carbon atom connected to phosphorus is replaced by a heteroatom, halogen substituted $C_6$-$C_{12}$ arylene, fused $C_6$-$C_{12}$ arylene, fused $C_6$-$C_{12}$ arylene, wherein the hydrogen atom connected to carbon is replaced by $C_6$-$C_{12}$ aryl, or a metal complex with a cycloalkylene as a ligand, wherein the cycloalkylene of the metal complex is bonded to a main chain of the polymer and phosphorus; $R_2$, $R_3$ and $R_4$ are, independently, $C_1$-$C_{10}$ alkyl, $C_3$-$C_8$ cycloalkyl or $C_6$-$C_{10}$ aryl; P represents phosphorus; X represents halogen; and n is an integer greater than 1 but less than 1500.

The polymer may optionally further include an inert repeat unit consisting vinyl monomers of formula II:

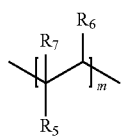

(II)

wherein $R_5$, and $R_6$ are independently hydrogen, an ester group, $C_1$-$C_{10}$ alkyl, $C_2$-$C_8$ alkenyl, $C_3$-$C_8$ cycloalkyl, 4 to 8 membered heterocyclic alkyl or $C_6$-$C_{10}$ aryl; $R_7$ is a hydrogen or $C_1$-$C_{10}$ alkyl; and m is an integer greater than 0 but less than 1500, more preferably 10-600.

The polymer is grafted onto the carbon nanomaterial by free radical polymerization, atom transfer radical polymerization (ATRP), reversible addition-fragmentation chain transfer polymerization (RAFT), ring-opening polyaddition (ROP), anion/cation polymerization or condensation, or combinations thereof. For the phosphonium-containing polymer synthesized by free radical polymerization, a polymer chain with a terminal free radical may be formed under appropriate conditions, which allows easy control of the structure and composition of the polymer coordinated catalyst as well as the polarity of the polymer chain when grafting the polymer to the heterogeneous carrier. The free radical polymerization may be used to synthesize a random copolymer as well as a block copolymer. In one embodiment of the present disclosure, the polymer has a repeat unit containing a phosphonium salt and the polymer has a number average molecular weight of 1,000-200,000, more preferably 5,000-80,000. The number of coordinated-catalyst can be regulated by the choice of the type and number of a functional monomer having a coordination function. In addition, the solubility of the coordinated-polymer in the reaction solution can be regulated through the adjustment of the proportion of the polar monomer (formula I) and the non-polar monomer (formula II). As such, the present disclosure may solve the problems of poor dispersibility of heterogeneous catalysts in organic solvents, and provides advantages of high catalytic reactivity as homogeneous catalysts and easy separation and recovery as heterogeneous catalysts, to improve the efficiency of catalyzation.

As an example, a random copolymer of general formula (III) can be obtained by a copolymerization of a biphenyl(4-vinyl benzene)phosphine (DPVP) monomer, styrene monomer, benzoyl peroxide (BPO) and tetramethyl piperidinyl oxy (TEMPO).

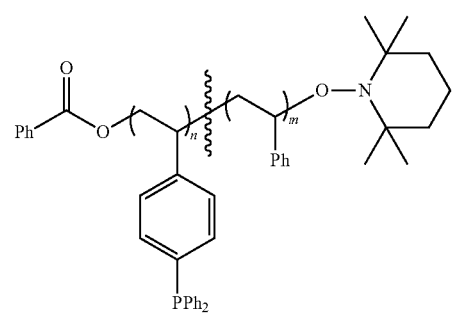

(III)

Then the polymer obtained is grafted onto the surface of the carbon nanomaterial, followed by a reaction with alkyl halide compound, thus providing a carbon nanomaterial-supported catalyst having phosphonium salt polymers (formula I and formula II).

Also as an example, a random copolymer as shown in formula (IV) can be obtained by atom transfer radical polymerization (ATRP), MMA monomer and a phosphine monomer (i.e. DPVP) in the presence of copper catalyst.

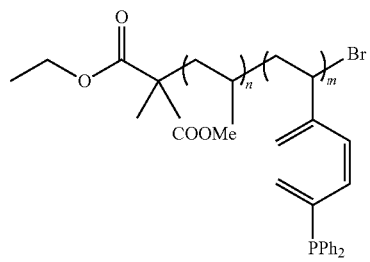

(IV)

Then the polymer obtained may be grafted onto the surface of the carbon nanomaterial by atom transfer radical polymerization (ATRP), followed by a reaction with alkyl halide compound, thus providing a carbon nanomaterial-supported catalyst having phosphonium salt polymers.

The carbon nanomaterial-supported catalyst of the present disclosure is particularly suitable for the cycloaddition reaction of carbon dioxide and an epoxy compound to form a carbonate. In one embodiment, the reaction may be performed as follows. The catalyst and the epoxy compound are placed in a high-pressure reactor, and then the reactor is purged and then filled with carbon dioxide. Then the reactants are introduced into the reactor under $CO_2$ atmosphere. The pressure of the reactor is controlled to be below 10 kg/cm$^2$ and the reactants in the reactor are heated and stirred. Then the reactor is cooled and pressure is released from the reactor. The reaction product is extracted by tetrahydrofuran (THF) and then filtrated. The filtrate is concentrated under a vacuum to obtain the products. In the preferred embodiment, the carbon nanomaterial-supported catalyst is added in an amount of more than 1%, more preferably from 3% to 40%, based on the total amount of the epoxy compound. The cycloaddition reaction is performed under a pressure below 150 atm, preferably 2-10 atm. In addition, the cycloaddition reaction is performed at a temperature below 200° C., preferably 50-120° C. In the preferred embodiment, the reaction yield can reach to at least 80% or more. Finally, after the reaction is completed, the mixture from the cycloaddition reaction is filtered. The filtrate was concentrated as product and the solid was recovered as the carbon nanomaterial-supported catalyst.

The following working examples confirm that the catalysts of the invention have properties of high catalytic reactivity and easy recovery in the cycloaddition reaction of carbon dioxide. The reaction has lower demand for production equipment, and may reduce the emissions of the unreacted carbon dioxide, and therefore is environmentally and economically advantageous.

Embodiments according to the present disclosure provide a synthesis method of carbonates, which may be used in a mixed solvent of an electrolyte in a lithium ion battery. Organic carbonate compounds used in these solvents like propylene carbonate (PC). In addition, the present method may also be applied in the chemical synthesis industry, to produce carbonate ester resins for applications in engineering plastics, such as automotive, electrical and electronic components. In addition, because the preparation method of the carbonate resin may avoid using highly toxic isocyanate esters, it can become a green material for non-isocyanate polyurethane resin, and can be used in biomedical materials.

Hereinafter, examples will be illustrated to explain the carbon nanomaterial-supported catalyst of the present disclosure in detail. Unless otherwise specified, all expressions of percentages are by weight.

Example 1

2,2,6,6-Tetramethylpiperidine-1-oxyl (TEMPO, 0.56 g, 3.6 mmol), benzoyl peroxide (BPO, 0.73 g, 3 mmol) and diphenyl(4-vinylphenyl)phosphine (DPVP, 22 g, 76.3 mmol) were placed into a 500 mL round-bottom reaction flask, and styrene (8.76 mL, 7.96 g, 76.4 mmol) and xylene (50 mL, pre-deoxygenated) were added together under a nitrogen atmosphere, resulting in an orange red solution. The solution obtained was stirred vigorously at a temperature of 95° C. for 3 hours. Hereafter, the solution was heated to a temperature of 130° C. with continuous stirring, and then the color of the solution gradually became dark brown. After 16 hours, the reaction was cooled down, and methyl alcohol (MeOH, 1000 mL, deoxygenated) was added to precipitate out the polymer. The solid was filtrated and vacuum-dried at a temperature of 45° C. for 16 hours, and then 16.3 g of a maize-yellow powder, $PDPVP_{50}$ was obtained (wherein the subscript "50" indicates that the molar ratio of DPVP and styrene was about 1:1, and the ICP-MS analysis of $PDPVP_{50}$ for the phosphorus content showed that the phosphorus monomer constituted 46% the structure of the polymer) (yield 54%). The random copolymer had a number average molecular weight of 12800, and a polydispersity index (PDI) of 1.69.

Example 2

Multiwall carbon nanotubes (MWNT, 1.5 g, $C_{Tube}$-100, $C_{Tube}$-200, $C_{Tube}$-300, manufactured by CNT Co., Ltd. KOREA) and $PDPVP_{50}$ (15.2 g) were placed into a reaction flask. Xylenes (500 ml) was added into the reaction flask by a syringe, followed by stirring of the solution continuously under a nitrogen atmosphere and at a high temperature of 130° C. for 48 hours. After the mixture was cooled to room temperature, tetrahydrofuran (THF; 100 mL) was added to dilute the solution. Hereafter, the solution was filtrated, and then the solid residue from the filtration was washed three times with THF (50 mL), and vacuum-dried to provide a black powder ($MWNT-PDPVP_{50}$; 1.4 g). The result of the XPS spectra shows a $P_{3p}$ (133 eV) signal, indicating that the surface of a carbon nanotube was grafted with the phosphorus-containing polymers. The result of the thermal gravimetric analysis (TGA) of the product ($MWNT-PDPVP_{50}$) showed that the polymer grafting amount of the carbon nanotube was 31.7%.

Example 3

$MWNT-PDPVP_{50}$ (0.262 g) was placed into a 50 mL reaction flask equipped with a condenser, and the reaction flask was purged with nitrogen (5 times). N-propyl bromide (270 mg, 200 μL, 2.20 mmol) and acetonitrile (10 mL, pre-deoxygenated) were injected via a syringe under a nitrogen atmosphere. The mixture was heated to reflux by an oil-bath. After 18 hours, the reaction mixture was cooled to room temperature and then filtrated. Hereafter, the solid residue on the filter was washed three times with THF (15 mL), and a black powder ($MWNT-PDPVP_{50}$-n-PrBr; 0.225 g; yield 86%) was obtained after vacuum drying.

Example 4

$MWNT-PDPVP_{50}$ (0.251 g) was placed into a 50 mL reaction flask equipped with a condenser, and the reaction flask was purged with nitrogen (5 times). Benzyl bromide (248 mg, 172 μL, 1.45 mmol) and acetonitrile (10 mL, pre-deoxygenated) were injected via a syringe under a nitrogen atmosphere. The mixture was heated to reflux by an oil-bath. After 18 hours, the reaction mixture was cooled to room temperature and then filtrated. Hereafter, the solid residue on the filter from the filtration was washed three times with THF (15 mL), and a black powder ($MWNT-PDPVP_{50}$-BzBr; 0.235 g; yield 94%) was obtained after vacuum drying. The result of the XPS spectra shows a $P_{3p}$ (133 eV) signal, indicating that the surface of a carbon nanotube was grafted with the phosphorus-containing polymers.

Example 5

$MWNT-PDPVP_{50}$ (0.205 g) was placed into a 50 mL reaction flask equipped with a condenser, and the reaction flask was purged with nitrogen (5 times). N-butyl chloride (n-BuCl, 177 mg, 200 μL, 1.86 mmol) and acetonitrile (10 mL, pre-deoxygenated) were injected via a syringe under a nitrogen atmosphere. The mixture was heated to reflux by an oil-bath. After 26 hours, the reaction mixture was cooled to room temperature and then filtrated. Hereafter, the solid residue on the filter from the filtration was washed three times with THF (15 mL), and a black powder ($MWNT-PDPVP_{50}$-BuCl; 0.195 g; yield 95%) was obtained after vacuum drying.

Example 6

$MWNT-PDPVP_{50}$ (0.210 g) was placed into a 50 mL reaction flask equipped with a condenser, and the reaction flask was purged with nitrogen (5 times). N-butyl iodine (n-BuI, 404 mg, 250 μL, 2.20 mmol) and acetonitrile (10 mL, pre-deoxygenated) were injected via a syringe under a nitrogen atmosphere. The mixture was heated to reflux by an oil-bath. After 26 hours, the reaction mixture was cooled to room temperature and then filtrated. Hereafter, the solid residue on the filter from the filtration was washed three times with THF (15 mL), and a black powder (MWNT-PDPVP$_{50}$-BuI; 0.193 g; yield 92%) was obtained after vacuum drying.

Example 7-15

(Typical procedure A) The reactor was purged with carbon dioxide five times. The reactor pressure was controlled at 3 kg/cm$^2$ at the fifth purging of carbon dioxide, and the pressure of the reactor was released while the reactor was maintained under atmosphere of carbon dioxide. The synthesized catalyst (200 mg; Examples 3-6) and the epoxy compound (10 mmol) were introduced into the reactor under $CO_2$ atmosphere. The mixture was stirred and heated at a temperature of 90° C. for a predetermined reaction time, and then the reactor was cooled immediately in ice water. The pressure of the cooled reactor was released, and then the product was extracted with tetrahydrofuran (THF) and then filtrated. The filtrate was concentrated under vacuum to obtain a yellow liquid (Examples 7, 9-15). The results of the GC-MS or NMR analysis of the product are listed in Table 1.

(Typical procedure B) The synthesized catalyst (200 mg; embodiments 3-6) and the epoxy compound (10 mmol) were placed into a high-pressure reactor. Hereafter, The reactor was purged with carbon dioxide five times. Then the reactor was controlled at a pressure of 3 kg/cm$^2$. The mixture was stirred and heated at a temperature of 90° C. for a predetermined time (see Table 1), and then the reactor was cooled immediately in ice water. The pressure of the cooled reactor was released and the product was extracted with tetrahydrofuran (THF) and then filtrated. The filtrate was concentrated under vacuum to obtain the grey-white solid (Example 8). The results of the GC-MS or NMR analysis of the product are listed in Table 1.

TABLE 1

| Example | catalyst | procedure | Reaction time (hr) | yield (%) | Structure of product |
| --- | --- | --- | --- | --- | --- |
| 7 | MWNT-PDPVP50-BzBr | A | 17 | 99 | |
| 8 | MWNT-PDPVP50-BzBr | B | 20 | 90 | |
| 9 | MWNT-PDPVP50-BzBr | A | 7 | 91 | |
| 10 | MWNT-PDPVP50-BzBr | A | 7 | 97 | |
| 11 | MWNT-PDPVP50-BzBr (recovered from Example 8) | A | 7 | 92 | |
| 12 | MWNT-PDPVP50-BzBr (recovered from Example 9) | A | 7 | 90 | |
| 13 | MWNT-PDPVP50-n-PrBr | A | 7 | 90 | |
| 14 | MWNT-PDPVP50-n-BuCl | A | 7 | 89 | |

TABLE 1-continued

| Example | catalyst | Reaction procedure | time (hr) | yield (%) | Structure of product |
|---|---|---|---|---|---|
| 15 | MWNT-PDPVP50-n-BuI | A | 7 | 83 | 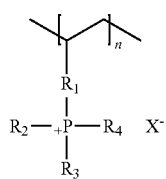 |

The conversion rate of epoxide was determined by $^1$H NMR

While the disclosure has been described by way of example and in terms of the above embodiments, it is to be understood that the invention is not limited to the disclosed embodiments. To the contrary, it is intended to cover various modifications and similar methods (as would be apparent to those skilled in the art). Therefore, the scope of the appended claims should be accorded the broadest interpretation so as to encompass all such modifications and similar methods.

What is claimed is:

1. A carbon nanomaterial-supported catalyst, comprising:
   (a) a carbon nanomaterial; and
   (b) a polymer grafted onto the carbon nanomaterial, wherein the polymer has a repeat unit containing a phosphonium salt and the polymer has a number average molecular weight of 1,000-200,000, wherein the repeat unit containing a phosphonium salt has a structure of formula I:

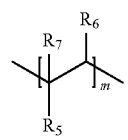

wherein $R_1$ represents $C_1$-$C_{10}$ alkylene, $C_3$-$C_8$ cycloolefin, $C_6$-$C_{12}$ arylene, an ester group, $C_3$-$C_8$ cycloalkene or $C_6$-$C_{12}$ arylene, wherein the carbon atom connected to phosphorus is replaced by a heteroatom, halogen substituted $C_6$-$C_{12}$ arylene, fused $C_6$-$C_{12}$ arylene, fused $C_6$-$C_{12}$ arylene, wherein the hydrogen atom connected to carbon is replaced by $C_6$-$C_{12}$ aryl, or a metal complex with a cycloalkylene as a ligand, wherein the cycloalkylene of the metal complex is bonded to a main chain of the polymer and phosphorus;
   $R_2$, $R_3$ and $R_4$ are, independently, $C_1$-$C_{10}$ alkyl, $C_3$-$C_8$ cycloalkyl or $C_6$-$C_{10}$ aryl;
   P represents phosphorus;
   X represents halogen; and
   n is an integer greater than 1 but less than 1500.

2. The carbon nanomaterial-supported catalyst of claim 1, wherein the carbon nanomaterial comprises: single-wall carbon nanotubes, multi-wall nanotubes, carbon nanofibers, carbon nanocapsules, active carbons, carbon blacks, or combinations thereof.

3. The carbon nanomaterial-supported catalyst of claim 1, wherein the polymer is grafted onto the carbon nanomaterial by free radical polymerization, atom transfer radical polymerization (ATRP), reversible addition-fragmentation chain transfer polymerization (RAFT), ring-opening polyaddition (ROP), anion/cation polymerization or condensation, or combinations thereof.

4. The carbon nanomaterial-supported catalyst of claim 1, wherein the polymer further comprises an inert repeat unit.

5. The carbon nanomaterial-supported catalyst of claim 4, wherein the inert repeat unit consists of polymerizable vinyl monomer.

6. The carbon nanomaterial-supported catalyst of claim 4, wherein the inert repeat unit has a structure of formula II:

$$\text{(II)}$$

wherein $R_5$, and $R_6$ are independently hydrogen, an ester group, $C_1$-$C_{10}$ alkyl, $C_2$-$C_8$ alkenyl, $C_3$-$C_8$ cycloalkyl, 4 to 8 membered heterocyclic alkyl or $C_6$-$C_{10}$ aryl;
   $R_7$ is a hydrogen or $C_1$-$C_{10}$ alkyl; and
   m is an integer greater than 0 but less than 1500.

7. A method of preparing carbonate, comprising:
   performing a cycloaddition reaction between a carbon dioxide and an epoxy compound in the presence of the carbon nanomaterial-supported catalyst of claim 1, to form a cyclic carbonate.

8. The method of claim 7, wherein the cycloaddition reaction is performed under a pressure below 150 atm.

9. The method of claim 7, wherein the cycloaddition reaction is performed at a temperature below 200° C.

10. The method of claim 7, wherein the carbon nanomaterial-supported catalyst is added in an amount of more than 1% by weight of the total amount of the epoxy compound.

11. The method of claim 7, further comprising filtering a product obtained from the cycloaddition reaction to recover and reuse the carbon nanomaterial-supported catalyst.

* * * * *